United States Patent [19]

Challberg et al.

[11] Patent Number: 4,822,742

[45] Date of Patent: Apr. 18, 1989

[54] REACTION TRAY FOR MEMBRANE HYBRIDIZATIONS

[75] Inventors: Sharon S. Challberg, Boyds; Randall Kiser, Frederick, both of Md.

[73] Assignee: Life Technologies, Inc., Gaithersburg, Md.

[21] Appl. No.: 48,421

[22] Filed: May 11, 1987

[51] Int. Cl.[4] .................................. C12M 1/00

[52] U.S. Cl. .................................. 435/310; 435/285

[58] Field of Search .............. 435/310, 285, 284, 296, 435/297, 298

[56] References Cited

U.S. PATENT DOCUMENTS

| | | | |
|---|---|---|---|
| 3,726,767 | 4/1973 | White | 435/285 |
| 3,745,091 | 7/1973 | McCormick | 435/285 |
| 4,294,924 | 10/1981 | Pepicelli et al. | 435/298 X |
| 4,321,330 | 3/1982 | Baker et al. | 435/284 X |
| 4,596,695 | 6/1986 | Cottingham . | |
| 4,598,050 | 7/1986 | Brown | 435/298 |
| 4,634,676 | 1/1987 | Sapatino | 435/298 X |

FOREIGN PATENT DOCUMENTS

| | | |
|---|---|---|
| 0032322 | 7/1981 | European Pat. Off. . |
| 1278005 | 10/1961 | France . |
| WO87/02386 | 4/1987 | World Int. Prop. O. . |

*Primary Examiner*—Larry Jones

*Attorney, Agent, or Firm*—Saidman, Sterne, Kessler & Goldstein

[57] ABSTRACT

A reaction tray specially suited for membrane hybridizations is disclosed. A tray 102 manufactured of firm but inexpensive material has a flat bottom. A firm but flexible overlay 106 is placed atop a membrane to evenly distribute a freely diffusing reactant, hinder evaporation, and avoid contamination. A lid 104 is friction fit onto the tray 102. The tray assembly 102/104/106 is floated on a water bath for the duration of the hybridization reaction. Manual handling of dangerous reactants and the delicate membrane is minimized. Low manufacturing costs allow the tray assembly to be disposable after a single use.

19 Claims, 1 Drawing Sheet

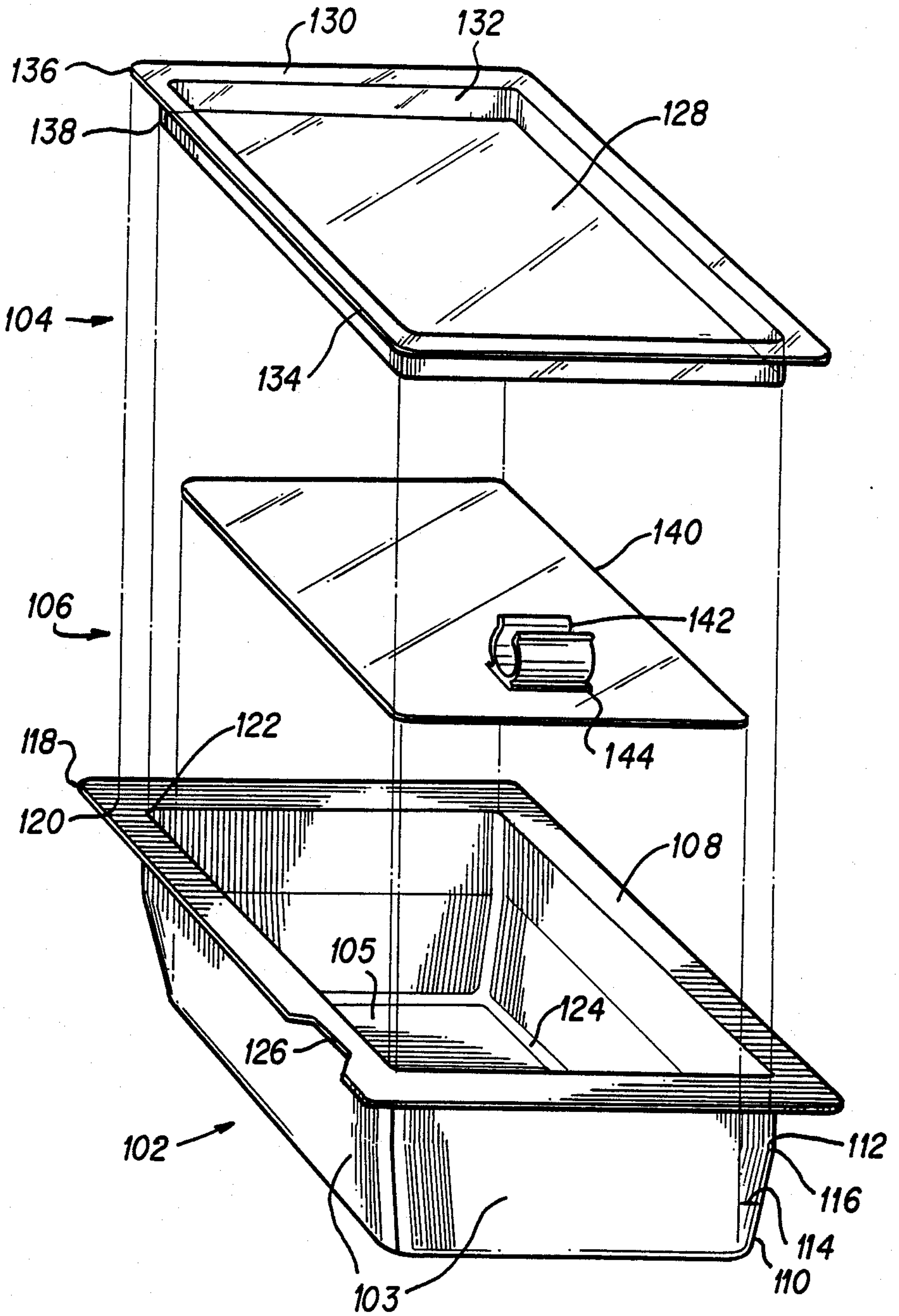
130
132
136
138
128
104
134
140
106
142
144
118
122
120
108
105
124
126
102
112
116
114
110
103

REACTION TRAY FOR MEMBRANE HYBRIDIZATIONS

BACKGROUND OF THE INVENTION

1. Field of the Invention

This invention relates to apparatus and methods for controlled chemical reactions which occur on a membrane. More specifically, the invention relates to apparatus and methods for performing reactions between a nucleic acid in solution and nucleic acid bound to a membrane.

2. Related Art

Apparatus and methods for the performance of hybridization reactions between nucleic acids in solution and nucleic acids bound to a membrane are known in the art.

One type of such system is exemplified by the "TURBO BLOT" (TM) Filter Processing System from American BioNuclear of Emeryville, CA. The device consists of a pouch containing a plastic mesh sleeve which surrounds a membrane which has, for example, various DNA samples immobilized at various loci on the membrane. The plastic envelope has ports through which fluids may be introduced or expelled. The plastic pouch is oriented substantially vertically on a slanted face of the device, with the ports at the top of the pouch. Reactants are introduced into and removed from the pouch through one of the ports by a syringe. The entire pouch assembly is mounted on a metallic frame. The entire assembly has to be manually removed to be placed in a water bath. After the desired reaction has occurred, a washing solution is thereafter introduced through one of the ports, and the wash solution is forced out the pouch's other port by a vacuum source.

Such devices possess the disadvantage of complexity of operation, bulkiness and high cost of manufacture. The device also requires a large amount of expensive reactant in order to properly bathe the membrane within the plastic pouch. Furthermore, there is an inherent difficulty in administering and removing the reactants and washing fluids with syringes and vacuum pumps. Also, the handling of the flexible pouch assembly presents a danger to personnel working with this known device. Since many of the reactants involved in hybridization research are radioactive, the possibility of spillage of the radioactive reactant presents a danger not only to personnel. The possibility of spillage also endangers the continued purity of various other chemicals in the laboratory.

In another known device, a flexible plastic bag containing the membrane with various loci having immobilized target reactants is heat-sealed after addition of the probe reactant. Scissors are used to open the bag after the reaction. Although the method employing the plastic bag is far less expensive than the above-described device employing syringes, it does not solve the problems of the susceptibility to puncture or tearing, or of its attendant dangers when radioactive reactants are being used. The manipulation of the flexible bag and the use of scissors in procedures involving radioactive reactants are issues of special concern. Furthermore, although the plastic bag method results in a decrease in the amount of expensive probe reactant which has to be used, more of that probe reactant is used than is actually necessary for performing the reaction.

What is therefore needed is an apparatus and method for carrying out chemical reactions on membranes in which the apparatus is easy and safe to use, minimizes the necessity of manual contact with potentially radioactive or otherwise dangerous reactants, reduces the volume of reactants needed, and is inexpensive to manufacture and simple to use.

SUMMARY OF THE INVENTION

The present invention overcomes the above-noted problems of known devices and techniques.

According to the present invention, a membrane or other chemical "target" medium is placed in the bottom of a tray manufactured of firm material. An overlay which is manufactured of firm but flexible material is placed over the membrane or target chemical when any of a probe reactant, wash buffer, blotting means, digestion agent, and so on, is allowed to diffuse toward the target reactant. The facial contour of the overlay matches that of the bottom of the tray so that the probe reactants (or other freely diffusing reactants) may freely and evenly diffuse to encounter the bound reactant. The firmness of both the overlay and the tray ensure a substantially uniform distribution of the freely diffusing reactants. Even distribution is not dependent on manual manipulation.

The edge of the overlay is shaped to substantially match the shape of the tray bottom's edge. This matching of edges facilitates the efficient distribution of reactants, and substantially reduces evaporation and contamination. The matched edges also help to prevent the escape of reactants into the surrounding laboratory environment. Prevention of such escape of reactants protects other chemicals in the laboratory from contamination, and protects laboratory personnel from danger. A handle may be placed on the upper face of the overlay so as to facilitate manual insertion and removal of the overlay with reduced possibility of human contact with the reactants.

In a second embodiment of the invention, a lid which substantially matches an upper opening of the tray may be used to further reduce evaporation (in longer reactions), as well as preventing contamination of, or contamination by, the reactants in the tray.

The invention may be constructed of materials so inexpensive that individual units may be considered disposable after a single use.

BRIEF DESCRIPTION OF THE DRAWINGS

The invention is best understood by reading the following detailed description in conjunction with the attached drawing.

The FIGURE represents an exploded view of the tray, overlay and lid in a preferred embodiment of the present invention.

DETAILED DESCRIPTION OF THE PREFERRED EMBODIMENTS

Structure of the Preferred Embodiment

The drawing shows the preferred embodiment of the present invention. There are three main components to the preferred embodiment.

A tray, generally indicated as 102, may be composed of opaque, white, high-impact styrene. It may be vacuum molded from, for example, 0.03 inch thickness high impact styrene or other material which is both strong enough to preserve its shape under normal handling, but still thin enough to readily conduct heat.

An overlay, generally indicated as 106, is adapted to fit snugly on the bottom 105 of tray 102. The overlay 106 may be constructed, for example, of transparent 0.01 inch thickness Type S mylar. The overlay may be die cut, and may be constructed of any inexpensive material which is firm but flexible. It may be manufactured of a material which is very inexpensive, but must return to its original shape after being bent momentarily.

A lid, generally indicated as 104, is adapted to fit snugly within the top of tray 102. The lid may be manufactured of, for example, 0.02-inch thickness polyvinyl chloride (PVC) and may be vacuum molded. The lid is advantageously manufactured of a transparent and inexpensive material, so long as it retains its shape through several insertions and removals from the top of tray 102.

To describe the preferred embodiment in more detail, tray 102 comprises a substantially flat bottom 105, four sides (two of which are indicated as 103), and a tray lip 108 which may traverse the top of all four sides. Tray bottom 105 is substantially flat, and has dimensions which are substantially determined by the size of the membrane (filter) which is to be placed on top of it in practicing the preferred method according to the present invention. Tray bottom 105 must be capable of readily transmitting heat, since the tray is floated on liquid baths of controlled temperature so as to allow the desired chemical process to occur.

Tray sides 103 project upwards from the edges of tray bottom 105. The figure indicates that four sides may be used to project upwardly from a substantially rectangular tray bottom 105, but it is to be understood that the invention may be embodied in a tray having any shape which may be appropriate to a particular application.

The slope of the sides 104 from the vertical are not critical to the invention, but may be chosen with practical criteria in mind. For example, the bottom 3.0 centimeters 110 of the preferred embodiment may be at a 5-degree draft 114. The upper 0.5 centimeters 116 may be at a 3-degree draft 112. Such a choice of drafts is advantageously chosen so as to facilitate the stacking of plural trays in storage. This choice of drafts also facilitates the simple and inexpensive manufacture of the apparatus.

Tray lip 108 extends around the top of the four sides 104 of the tray in the preferred embodiment. Tray lip 108 facilitates the handling of the tray 102 while minimizing the distorting effect of such handling on the shape of tray bottom 105. A finger notch 126 is advantageously employed along the lip 108 near a corner to facilitate the removal of lid 104 (described immediately below) from tray 102.

As can be seen from the figure, the three components of the preferred embodiment fit together in a straightforward fashion.

The dimensions of overlay 106 are determined by the dimensions of tray bottom 105. The cost of manufacturing the overlay may be reduced by allowing a reasonable tolerance, typically 1–2 mm on all four sides, between the outer edge 140 of overlay 106 and the edge 124 of tray bottom 105.

Overlay 106 and tray bottom 105 should have matching faces. In the preferred embodiment, faces of both overlay 106 and tray bottom 105 are flat. This matching of faces allows the two pieces to fit snugly together and maintain a substantially uniform thickness of liquid reactants when the overlay 106 is left atop the reactants in tray bottom 105. The overlay should be flexible so as to allow laboratory personnel to insert first one edge of the overlay 106 into one edge of tray bottom 105, and then "roll" the bubbles out of the reactants as the overlay 106 is slowly pressed down in its entirety.

A handle 142 is advantageously placed near one end of overlay 106 so as to facilitate this "rolling" of the bubbles out of the reactants on the membrane. The handle itself may be advantageously manufactured of PVC. The handle 142 is attached to overlay 106 at a point 144 by a fixative which is inert with respect to any chemical reactions which may take place in the planned experiment. This handle 142 facilitates the ability of the overlay 106 to evenly distribute reactants, as well as encourage the absorption of fluids when a blotter is being applied to the membrane.

Overlay 106 serves also to reduce evaporation of the reactants. Overlay 106 also helps to prevent the splashing of droplets of reactants out of tray 102, and helps to prevent the introduction of contaminants from outside tray 102. The location of handle 142 on the overlay 106 separates the potentially dangerous reactants from the potentially contaminating fingers of laboratory personnel.

The preferred embodiment of lid 104 comprises a face 128, a lid vertical edge 132, and a lip 130. The outside 138 of vertical edge 132 is preferably designed to fit snugly at 122 within the top of tray 102. The outer vertical edge 138 of the lid may be manufactured so as to be friction-fit within the top of tray 102 when inserted at 122. This friction-fit seal ensures that reactants do not escape. This seal also ensures that contaminants do not enter the tray. In longer-duration reactions, the lid further deters the evaporation of reactants. In most applications, the seal between the outer vertical edge 138 of lid 104 and the inner surface 122 of tray 102 needs to be substantially fluid tight. The presence of lip 130 on lid 104 further ensures that reactants do not escape and contaminants do not enter.

The friction-fit seal is effectuated by matching the draft of lid outer edge 138 to the draft of the top of the tray's walls, as was indicated at 112. In the preferred embodiment, this common draft was chosen to be 3 degrees.

The lip 130 of lid 104 does not extend outwardly as far as tray lip 108 in the preferred embodiment. This ensures that when laboratory personnel lift the entire tray assembly comprising tray 102, overlay 106, and lid 104, their fingers touch only tray lip 108. Their fingers do not likely touch lip 130 so as not to disturb the substantially fluid-tight seal between lid 104 and tray 102.

Lip 130 should extend outward far enough at 134 to protrude over finger notch 126 so as to facilitate the deliberate removal of lid 104.

Practicing a Preferred Method of the Invention

The following detailed description of a method practiced according to the present invention is specifically directed to tests for human papillomavirus DNA, which is generally thought to be a cause of human cervical cancer. Of course, many other reaction techniques can be practiced while still remaining within the scope of the present invention. The present invention does find special utility in membrane hybridization reactions such as the one which will be described below.

It should be understood that in this discussion, and in the claims which follow it, the term "reactant" is used broadly. A variety of applications where a chemical reaction need not actually occur lies within the contemplation of the present invention.

Before practicing the following exemplary method according to the present invention, it is assumed that a membrane (filter) has been prepared for a hybridization reaction. Different samples of DNA from different patients may be placed at the various loci on the membrane. This DNA is referred to as an immobilized reactant, inasmuch as it is bound to the membrane. It may also be called a target reactant.

Other chemicals, such as nucleic acid in solution, are generally termed freely diffusing reactants, or probe reactants. Probe reactants are generally expensive, and a substantial reduction in the amount of probe reactant which is necessary for a given test is achieved by the present invention. Also, reduction in the handling of the membrane, and elimination of the direct manual manipulation of the reactants is achieved according to the above-described apparatus utilized in the following method.

A very specific, exemplary method according to the present invention is described by the following steps:

The membrane is placed in the tray.

5 ml of pre-hybridization mix (blocking agent) is added (for example, by pipet) onto the membrane.

The overlay is "rolled" over the wet membrane, evenly dispersing the blocking agent.

The lid is placed on the tray.

The tray assembly (tray, membrane, overlay, and lid) is floated atop a 60° C. water bath for 15 minutes.

The tray assembly is removed from the water bath.

The lid is removed.

The overlay is removed.

An absorbent blotting pad (for example, 320-200 from Eaton-Dikeman) is placed atop the wet membrane to absorb the pre-hybridization solution for 15–20 seconds, optionally with pressure applied using the overlay. The blotting pad is removed by, for example, tweezers, and is discarded.

1.5 ml of hybridization solution (probe) is added (for example, by pipet) onto the surface of the membrane.

The overlay is "rolled" onto the membrane to evenly distribute the probe, and to prevent evaporation and contamination.

The lid is placed on the tray.

The tray assembly is placed atop a 60° C. water bath for 2 hours. (Of course, the time duration of this incubation depends on the particular probe, target, and membrane involved.)

The tray assembly is removed from the water bath.

The lid is removed.

The overlay is removed.

A blotting pad is added to the wet membrane to absorb the hybridization mix (probe). The overlay may be used to assist in the blotting. The overlay may then be discarded.

50 ml of wash reagent is added to the tray.

The lid is placed on the tray.

The tray assembly is slowly agitated for 2 minutes at room temperature. The liquid wash buffer is discarded. These washing steps are repeated two more times.

In this particular embodiment of the method, 15 ml of digestion agent (for example, 50 micrograms/ml RNAseA) is added to the tray.

The lid is placed on the tray.

The tray assembly is partially submerged in a 37° C. water bath for 15 minutes.

The lid is removed.

The digestion agent is discarded.

125 ml of pre-heated 60° C. wash buffer is added to the tray.

The lid is placed on the tray.

The tray assembly is partially submerged in a shaking 60° C. water bath for 5 minutes.

The lid is removed.

The liquid is discarded. The washing steps are repeated two times.

The lid is removed.

The membrane is removed.

The tray and lid may be discarded, or may be used a limited number of times, until the shapes of the tray assembly components have been deformed through use.

It should be noted that the handling (and thus contamination) of the membrane is substantially eliminated since it remains substantially motionless in the tray throughout all the steps prior to autoradiography. Also, danger of damage to the delicate membrane is thereby substantially minimized.

Although the present invention is specially suitable for use in hybridization reactions such as are involved in the isolation of the human papillomavirus, it can be used in any application where proper distribution of reagents needs to be inexpensively achieved with a minimum of danger of contamination or spillage, minimum damage to membranes, or prevention of injury to laboratory personnel. For example, incubations of antibodies with western blots may be performed. Solid phase supports may be processed, through hybridization and detection. The tray itself may be used as an inexpensive washing and processing station for membranes. Thus, the scope of the present invention should not be limited by the exemplary embodiments described above, but should be defined only in accordance with the following claims.

What is claimed is:

1. An apparatus for facilitating chemical reactions involving a target reactant means and a freely diffusing reactant, the apparatus comprising:

the target reactant means;

a tray with a tray bottom for supporting the target reactant means; and an overlay for insertion into said tray atop the target reactant means;

wherein a face of said overlay is matched to a face of said tray bottom so as to substantially evenly distribute the freely diffusing reactant.

2. The apparatus according to claim 1, wherein both said overlay face and said tray bottom face are substantially flat.

3. The apparatus according to claim 1, wherein:

the shape of said overlay substantially matches the shape of said tray bottom;

whereby evaporation of reactants may be reduced and contamination may be prevented.

4. The apparatus according to claim 1, further comprising:

a lid for covering said tray so as to ensure a substantially fluid-tight seal.

5. The apparatus according to claim 4, wherein said lid fits into said tray by means of a friction-fit seal.

6. The apparatus according to claim 4, wherein:

said tray and said lid have respective lips; and said lip of said lid is narrower than said lip of said tray.

7. The apparatus according to claim 4, wherein:

said tray, said overlay, and said lid are manufactured of materials so inexpensive that they are disposable after use.

8. The apparatus according to claim 1, wherein: said tray and said overlay are manufactured of materials which are so inexpensive that they are disposable after a single use.

9. The apparatus according to claim 1, wherein:
said tray may be floated on a water bath; and
said tray bottom conducts heat so as to facilitate a chemical reaction between said target reactant means and said freely diffusing reactant.

10. The apparatus according to claim 1, wherein: said overlay comprises a handle means whereby even distribution of said freely diffusing reactant is facilitated without direct manual manipulation by a person inserting said overlay.

11. The apparatus according to claim 1, wherein: said overlay is a flexible overlay.

12. A method for carrying out a chemical reaction involving a target reactant means and a freely diffusing reactant, the method comprising the steps of:
placing the target reactant means in the bottom of a tray;
adding the freely diffusing reactant to the target reactant means;
placing an overlay atop the target reactant means so as to substantially evenly distribute the freely diffusing reactant over the target reactant means; and
allowing the chemical reaction, if any, between the target reactant means and the freely diffusing reactant to occur.

13. The method according to claim 11, further comprising the step of:
floating said tray on a water bath so as to facilitate a chemical reaction.

14. The method according to claim 11, further comprising the step of:
placing a lid upon said tray.

15. The method according to claim 11, further comprising the steps of:
removing said overlay from said tray; and
adding a washing reagent to said target reactant means in said tray.

16. The method according to claim 11, wherein:
said target reactant means remains substantially motionless within said tray throughout all steps in said chemical reaction.

17. The method according to claim 11, wherein said step of placing an overlay comprises:
rolling a flexible overlay onto the target reactant means so as to substantially evenly distribute the freely diffusing reactant over the target reactant means.

18. A method of conducting a membrane hybridization reaction, comprising the steps of:
placing a membrane in a tray;
adding a predetermined volume of blocking agent to said membrane;
rolling an overlay over said wet membrane so as to evenly disperse said blocking agent;
placing a lid on said tray;
floating a tray assembly comprising said tray, said membrane, said overlay, and said lid atop a water bath for a first predetermined time duration;
removing said tray assembly from said water bath;
removing said lid from said tray;
removing said overlay from said tray;
placing an absorbent blotting pad a top said wet membrane so as to absorb said blocking agent;
removing said blotting pad from said tray;
discarding said blotting pad;
adding a predetermined volume of probe reactant to said membrane;
rolling said overlay onto said membrane so as to evenly disperse said probe and prevent evaporation and contamination;
placing said lid on said tray;
placing said tray assembly atop a water bath for a second predetermined time duration;
removing said tray assembly from said water bath;
removing said lid from said tray;
removing said overlay from said tray;
adding a blotting pad to said wet membrane to absorb said probe reactant;
discarding said blotting pad and said overlay;
adding a predetermined amount of wash reagent to said tray;
placing said lid on said tray;
agitating said tray assembly for a third predetermined time duration;
discarding said wash buffer;
repeating the four most recent steps a predetermined number of times;
adding a predetermined quantity of a digestion agent to said membrane in said tray;
placing said lid on said tray;
partially submerging said tray assembly in a water bath for a fourth predetermined time duration;
removing said lid from said tray;
discarding said digestion agent;
adding a predetermined quantity of heated wash buffer to said tray;
placing said lid on said tray;
floating said tray assembly atop a shaking water bath for a fifth predetermined time duration;
removing said lid from said tray;
discarding said wash buffer;
repeating the five most recent steps a predetermined number of times; and
removing said membrane.

19. An apparatus for facilitating chemical reactions involving a target reactant means and a freely diffusing reactant, the apparatus comprising:
the target reactant means;
a tray with a tray bottom for supporting the target reactant means;
an overlay for insertion into said tray atop the target reactant means to substantially evenly distribute the freely diffusing reactant; and
a lid for covering said tray so as to insure a substantially fluid-tight seal;
wherein said lid fits into said tray by means of a friction-fit seal.

* * * * *